(12) United States Patent  
Siebrecht et al.

(10) Patent No.: US 8,795,183 B2  
(45) Date of Patent: Aug. 5, 2014

(54) HANDPIECE FOR ULTRASONIC MEDICAL DEVICES INCLUDING SEAL FOR MECHANICAL ISOLATION OF ULTRASONIC DRIVER ASSEMBLY

(75) Inventors: Wayne A. Siebrecht, Golden, CO (US); David J. Wesley, Lyons, CO (US); David B. Mogill, Westminster, CO (US); Daniel S. Goldberger, Boulder, CO (US)

(73) Assignee: Sound Surgical Technologies LLC, Hayward, CA (US)

( * ) Notice: Subject to any disclaimer, the term of this patent is extended or adjusted under 35 U.S.C. 154(b) by 821 days.

(21) Appl. No.: 12/965,632

(22) Filed: Dec. 10, 2010

(65) Prior Publication Data

US 2011/0196266 A1    Aug. 11, 2011

Related U.S. Application Data

(60) Provisional application No. 61/285,508, filed on Dec. 10, 2009.

(51) Int. Cl.  
*A61B 8/00* (2006.01)

(52) U.S. Cl.  
USPC .......................................................... 600/459

(58) Field of Classification Search  
None  
See application file for complete search history.

(56) References Cited

U.S. PATENT DOCUMENTS

| | | | | |
|---|---|---|---|---|
| 8,118,743 | B2 * | 2/2012 | Park et al. ..................... | 600/437 |
| 8,562,535 | B2 * | 10/2013 | Driedger ....................... | 600/462 |
| 2007/0276241 | A1 * | 11/2007 | Park et al. ..................... | 600/437 |

* cited by examiner

*Primary Examiner* — Unsu Jung  
*Assistant Examiner* — Amanda Lauritzen Moher  
(74) *Attorney, Agent, or Firm* — Wood, Herron & Evans LLP

(57) ABSTRACT

Described are embodiments including methods and devices for venting a handpiece of a medical device. These embodiments provide a vent for the handpiece. A porous membrane is positioned over an opening of the vent to allow gas, including steam, to enter and escape from the handpiece and prevent liquids from entering the handpiece. Other embodiments include methods and devices for holding an ultrasonic driver assembly within a handpiece and preventing the ultrasonic driver assembly from rotating within the handpiece. These embodiments include positioning the ultrasonic driver assembly such that the ultrasonic driver assembly is held in place at a node of the ultrasonic driver assembly and an anti-rotation mechanism is also located at the node.

8 Claims, 13 Drawing Sheets

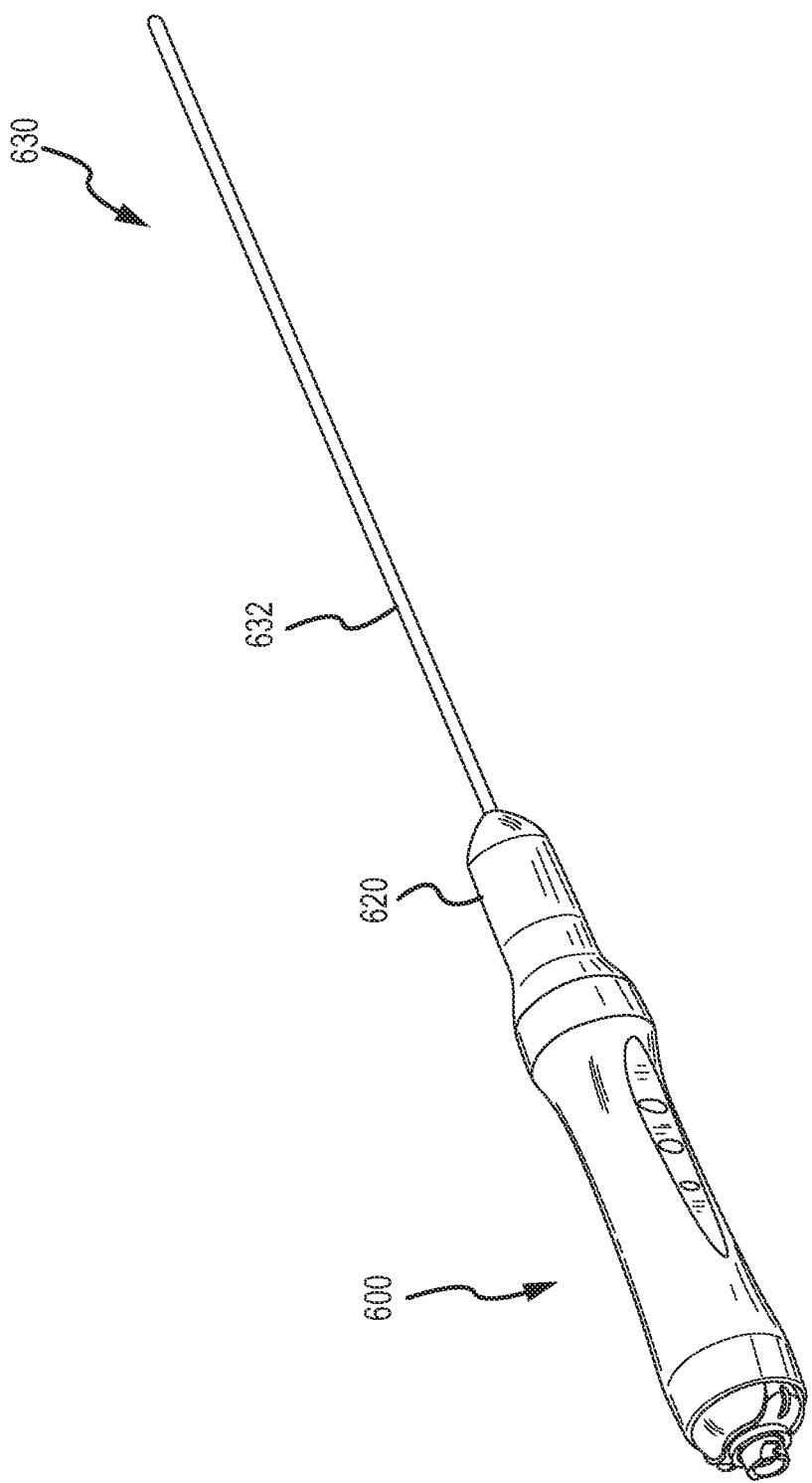

HANDPIECE FOR ULTRASONIC MEDICAL DEVICES INCLUDING SEAL FOR MECHANICAL ISOLATION OF ULTRASONIC DRIVER ASSEMBLY

CROSS-REFERENCE TO RELATED APPLICATIONS

This application claims priority to U.S. Provisional Patent Application No. 61/285,508 filed on Dec. 10, 2009, entitled MEDICAL DEVICE HANDPIECE, which is hereby incorporated by reference in its entirety as if set forth herein in full.

BACKGROUND

Medical devices for surgical procedures such as lipoplasty typically include a handpiece that allow surgeons to easily hold and manipulate the medical device when using the device during a medical procedure. Medical devices used in lipoplasty include ultrasonic probe assemblies and cannulas.

Ultrasonic probes are available in different shapes and sizes for emulsifying adipose tissue in different parts of the body. An ultrasonic driver assembly is typically included within a handpiece with various probes able to be connected to the ultrasonic driver and handpiece. The probes are typically threaded on one end and engage threads on the ultrasonic driver. When engaging the probe with the driver the probe is tightened to ensure good mechanical coupling. During tightening, the ultrasonic driver assembly may rotate within the handpiece causing wires that power the assembly to twist. Repeated rotation of the ultrasonic driver assembly to connect and disconnect various probes results in broken wires and shorting of the ultrasonic driver assembly.

Medical devices that are reused, such as handpieces, must be sterilized before each use. Sterilization typically is performed using steam within a pressurized autoclave. The steam kills microorganisms such as bacteria and viruses. After the sterilization process, a dry cycle is performed to eliminate any trapped moisture that remains from the steam, such as may occur within a handpiece with an ultrasonic driver assembly. Medical professionals do not always follow the appropriate procedures to ensure that all of the trapped moisture is removed during the dry cycle. The resulting condensation from the trapped humidity may create corrosion problems or other damage to electrical or other components of the medical device.

Embodiments of the present invention have been made in light of these and other considerations. However, the relatively specific problems discussed above do not limit the applicability of the embodiments of the present invention.

SUMMARY

The summary is provided to introduce aspects of some embodiments of the present invention in a simplified form, and is not intended to identify key or essential elements of the claimed invention, nor is it intended to limit the scope of the claims.

Embodiments of the present invention include methods and devices for holding an ultrasonic driver assembly within a handpiece and preventing the ultrasonic driver assembly from rotating within the handpiece. Embodiments include positioning the ultrasonic driver assembly such that the ultrasonic driver assembly is held in place at a vibrational node of the ultrasonic driver assembly. A mechanism is then provided at the node of the ultrasonic driver assembly to limit the rotation of the driver assembly within the handpiece.

Other embodiments of the present invention are directed to methods and devices for venting a handpiece of a medical device. These embodiments provide a vent for the handpiece. A porous membrane is positioned over an opening of the vent to allow gas, including steam, to enter and escape from the handpiece and prevent liquids from entering the handpiece.

BRIEF DESCRIPTION OF THE DRAWINGS

Non-limiting and non-exhaustive embodiments are described with reference to the following figures.

FIG. 12 illustrates an ultrasonic probe assembly with a nosecone having a different design than shown in FIG. 8.

DETAILED DESCRIPTION

Principles and features of the present invention may be further understood by reference to the following detailed description and the embodiments depicted in the accompanying drawings. It should be understood that although specific features are shown and described below with respect to detailed embodiments, the present invention is not limited to the embodiments described below.

Figure 1:
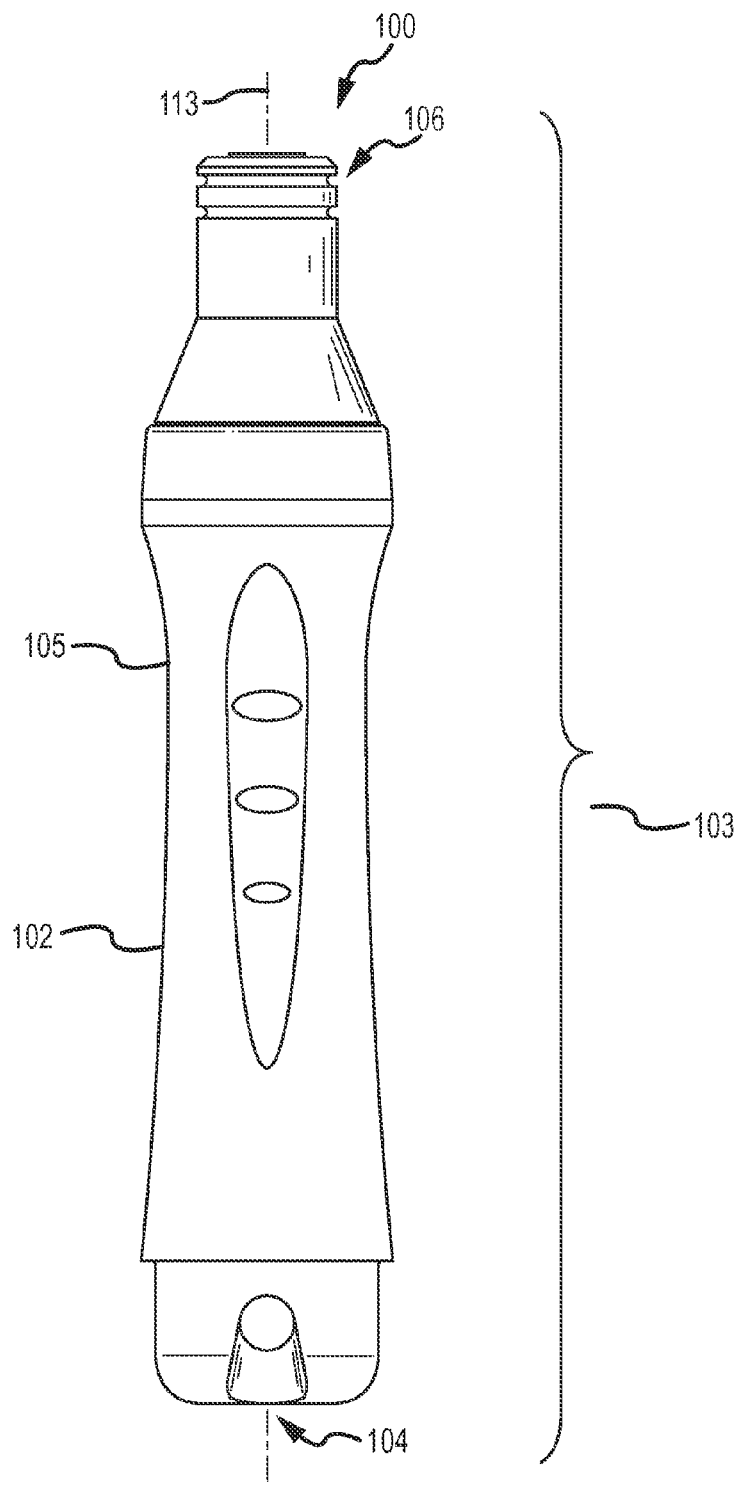
FIG. 1 illustrates a perspective view of a handpiece according to an embodiment of the present invention.

FIG. 1 illustrates a front view of a handpiece 100 for a medical device according to an embodiment of the present invention. As described in further detail below, handpiece 100 is hollow and includes an interior volume. Handpiece 100 includes a sidewall 102 that extends vertically to create an elongated piece 103 with a proximate end 104 and a distal end 106. In the embodiment shown in FIG. 1, the side wall 102 forms an enclosed body that includes an interior volume 118 (see FIG. 2 below). In one embodiment, handpiece 100 is part of an ultrasonic probe assembly that includes an ultrasonic driver assembly within handpiece 100 and an ultrasonic probe connected to the ultrasonic driver assembly. The ultrasonic probe assembly may be used in ultrasonic assisted lipoplasty (UAL) procedures such as those procedures performed using the VASER® UAL system commercially available from Sound Surgical Technologies LLC in Louisville, Colo.

As shown in FIG. 1, an outer surface 105 of sidewall 102, handpiece 100 may include ergonomic features to accommodate a surgeon's hand and fingers. In one embodiment, the ergonomic features may be formed by a cover that is placed on the outer surface 105 of sidewall 102. In other embodiments, sidewall 102 may be molded so that the ergonomic features are formed as part of the outer surface 105. In yet other embodiments, the ergonomic features may be a combination of features formed as part of outer surface 105 and additional material such as a cover placed over outer surface 105.

In one embodiment, a cover placed over outer surface 102 is individually customized to a surgeon's hand. In these embodiments, an impression of a surgeon's hand is first obtained. A temporary soft material, such as modeling clay, is placed over the outer surface 105 and the surgeon may shape the soft material to fit his/her hand shape or his/her particular finger placement for best comfort. This temporary soft material's shape is then scanned using a 3-D scanner such as NextEngine HD 3D Scanner, manufactured by NextEngine, Inc. of Santa Monica, Calif. This 3-D scanned image is then used with the CAD model to create a computer model of the soft material. From this computer model tooling, an outer cover or part is designed and molded for use on the handpiece 100. The cover or part can then be placed on outer surface 105. In embodiments, the cover or part can be made from materials such as silicone.

Figure 2:
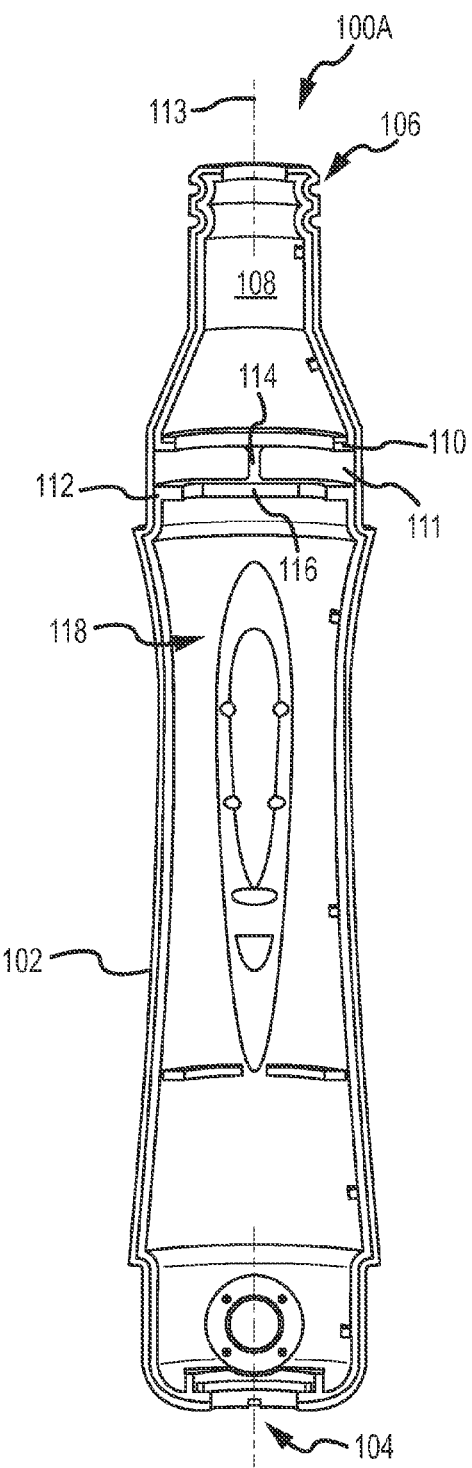
FIG. 2 illustrates a cross-section of the handpiece illustrated in FIG. 1 according to an embodiment of the present invention.
Figure 5:
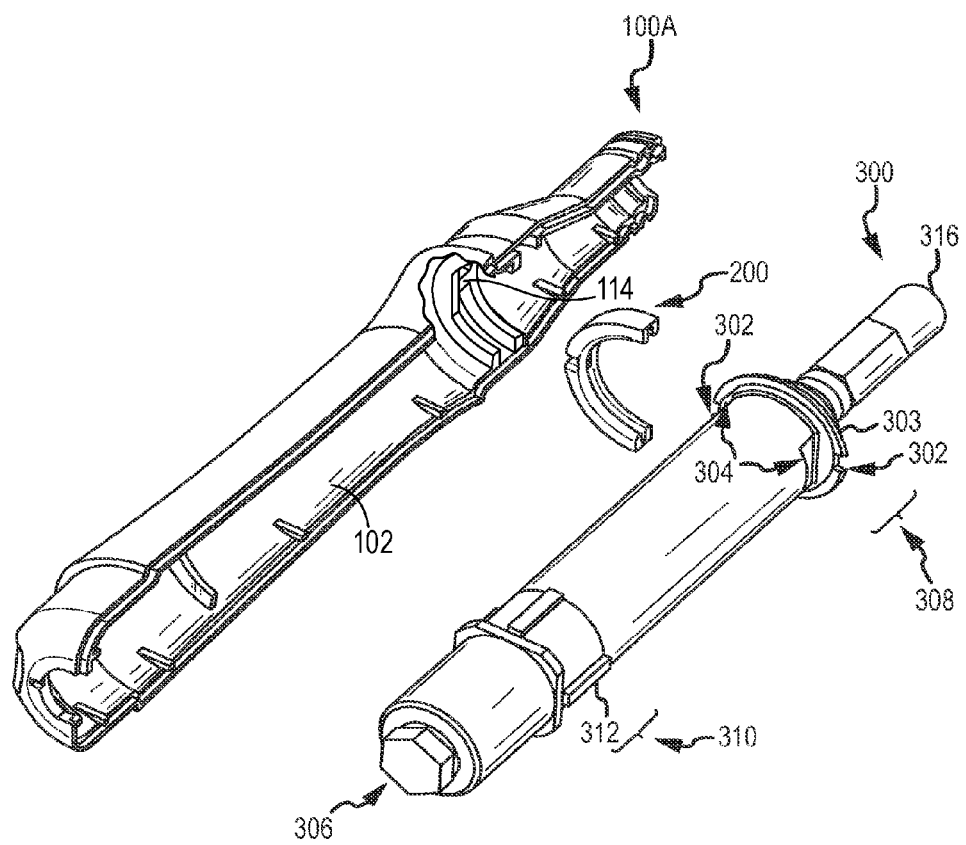
FIG. 5 illustrates an expanded view of the cross-section shown in FIG. 2, the seal shown in FIG. 4 and a driver assembly according to an embodiment of the present invention.

FIG. 2 illustrates a cross-section 100A of the handpiece 100 illustrated in FIG. 1. FIG. 2 shows interior volume 118. Interior volume 118 is designed to hold at least some of the components of a medical device such as an ultrasonic driver assembly, as shown in FIG. 5 and described below. Although the description below describes an embodiment of using handpiece 100 to hold an ultrasonic driver assembly for use with an ultrasonic probe, such as used in lipoplasty procedures, those with skill in the art will appreciate that the present invention is not limited to this embodiment and features described below may, in other embodiments, be used with other medical devices.

In some embodiments, handpiece 100. and side wall 102, is machined from a single piece of material, such as a polymer. In other embodiments, handpiece 100 (FIG. 1), and side wall 102, is made from two cross-sectional pieces each as described below with respect to cross-section 100A. The two cross-sectional pieces are connected and secured, for example, by a ring positioned around both cross-sectional pieces. In those embodiments in which the cross-sectional pieces are made of a polymer, the cross-sectional pieces can be joined together by being solvent welded together to join the two cross-sectional pieces. Solvent welding is the process of applying a solvent to join articles made from polymer. The solvent dissolves polymer at the interface of the articles to be joined. The dissolved polymer from the articles can flow and mingle together. When the solvent evaporates, a solid mass of polymer (i.e., the weld) connecting the articles remains.

Some non-limiting examples of polymers that may be used as "welding solvents" to make handpiece 100 include, but are not limited to, medical grade polyphenylene oxide (PPO); polystyrene (PS); polyphenylsulfone (PPSU) and combinations thereof. In one embodiment, a PPO polymer sold under the trade name Noryl® by SABIC Americas, Inc., Houston, Tex. may be used. In other embodiments, a PPSU polymer sold under the trade name Radel® by Solvay Advanced Polymers, L.L.C., Alpharetta, Ga. may be used.

Different solvents or adhesives can be used to join the two cross-sectional pieces. The specific solvent or adhesive will depend upon the polymer used to make the cross-sectional pieces of handpiece 100. One non-limiting example of a solvent that may be used in some embodiments to solvent weld two cross-sectional pieces made of polymer is trichloroethylene. In other embodiments, two cross-sectional pieces made of polymer may be joined using an epoxy adhesive. In one embodiment, epoxy adhesives sold under the trade names BONDiT™ B-45 and BONDiT™ B-45TH by Reltek, L.L.C. of Santa Rosa, Calif. may be used.

Figure 3:
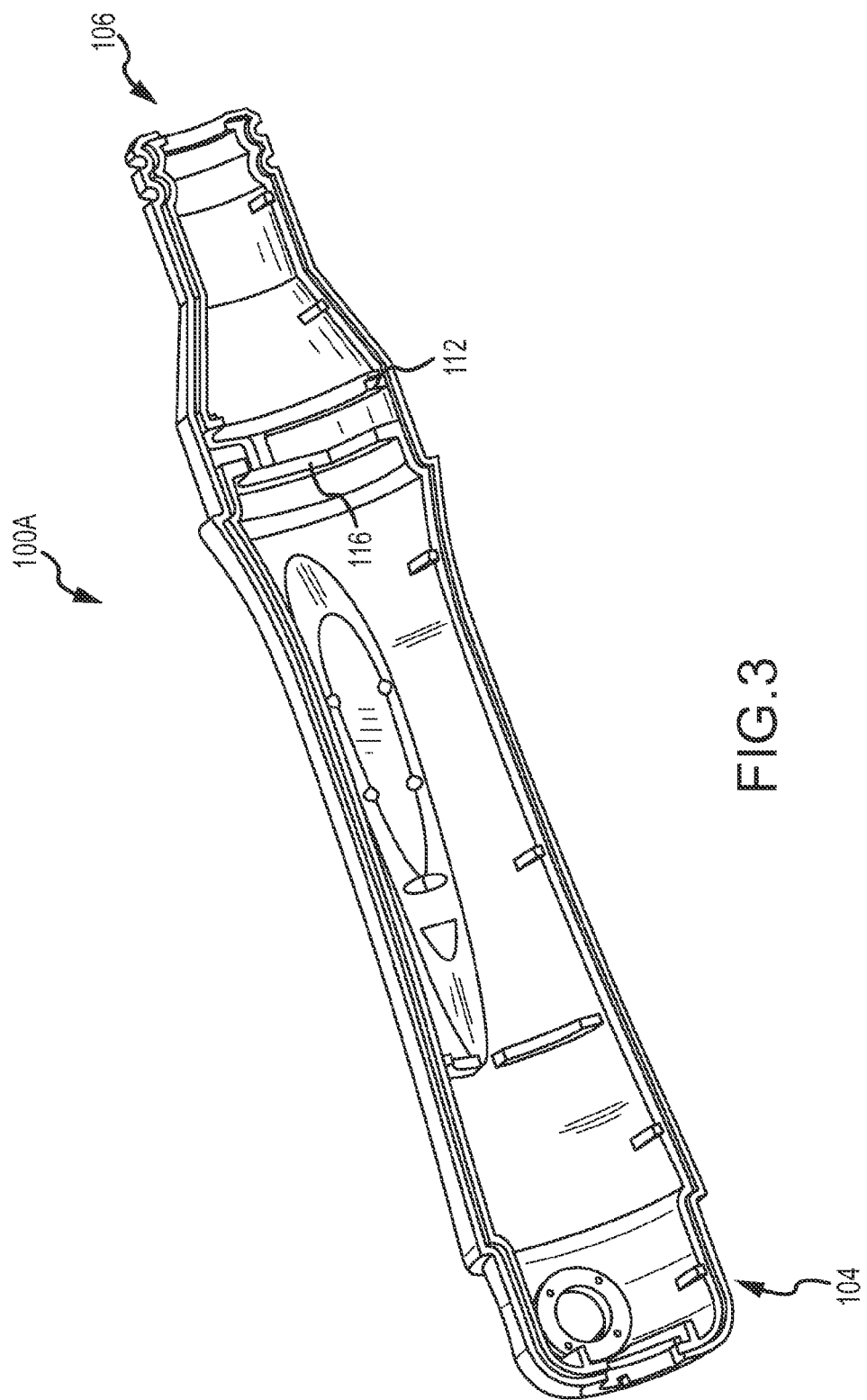
FIG. 3 illustrates a perspective view of the cross-section shown in FIG. 2 that better illustrates some features of the handpiece according to an embodiment of the present invention.

Referring again to FIG. 2, an inner surface 108 of side wall 102 is shown. Inner surface 108 includes a first ridge 110 and a second ridge 112 that is substantially parallel to the first ridge 110. In the embodiment shown in FIGS. 2 and 3, ridges 110 and 112 are substantially orthogonal to a central axis 113 of handpiece 100 (FIG. 1). A channel 111 is formed between ridge 110 and 112. Inner surface 108 also include a ridge 114 that is within channel 111 and substantially orthogonal to ridges 110 and 112. As described in greater detail below, ridges 110, 112, and 114 are used to hold an ultrasonic driver assembly within interior volume 118 and limit the rotation of the ultrasonic driver assembly within handpiece 100. Also shown in FIG. 2 is flat area 116 on ridge 112. In embodiments, flat area 116 is used as a stop to help limit the rotation of the ultrasonic driver assembly in interior volume 118. FIG. 3 illustrates a perspective view of the cross-section 100A shown in FIG. 2 that better illustrates the ridges 110 and 112 the flat area 116 on ridge 112.

Figure 4:
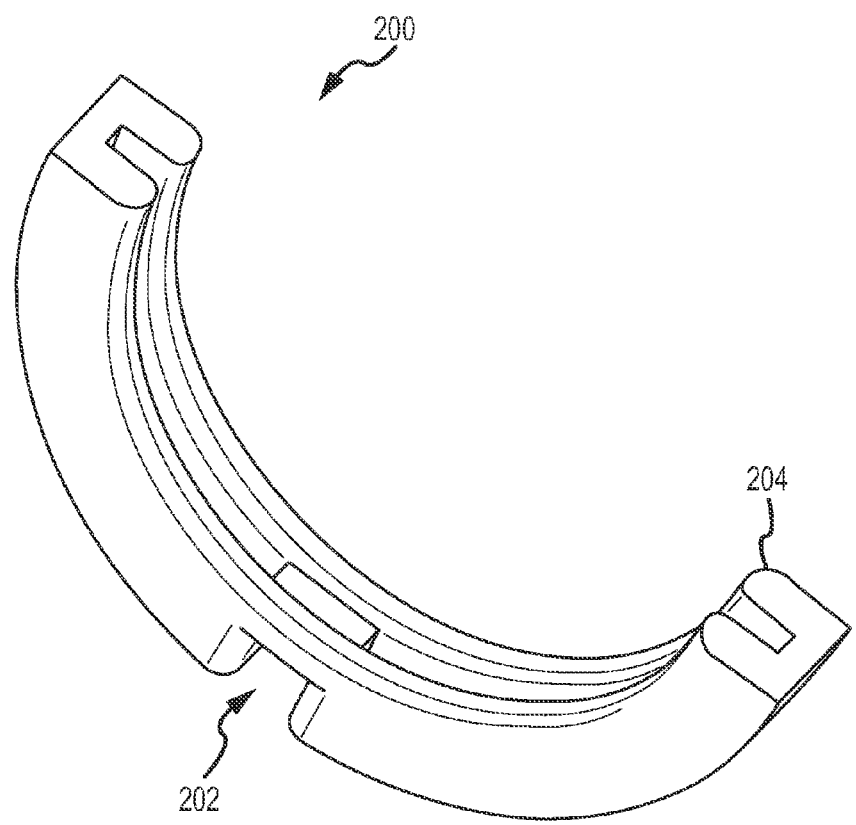
FIG. 4 illustrates a seal for acoustically isolating an ultrasonic driver assembly from the handpiece according to an embodiment of the present invention.

FIG. 4 illustrates a seal 200 for mechanically isolating an ultrasonic driver assembly that is positioned within volume 118 from the side wall 102 of handpiece 100. The seal is positioned within channel 111 shown in FIG. 2. Seal 200 includes a notch 202 for engaging with the ridge 114 on inner surface 108 (FIG. 2). Seal 200 also includes a channel 204 for engaging with a portion of the ultrasonic driver assembly.

Seal 200 may be made from any mechanically dampening material such as foams or rubbers. In one specific embodiment, seal 200 is made from thermal plastic elastomer such as Santopreme™.

FIG. 5 illustrates an exploded view of the cross-section 100A shown in FIG. 2, the seal shown in FIG. 4 and an ultrasonic driver assembly 300. FIG. 5 illustrates how the seal 200 engages with the cross section 100A of handpiece 100 and the driver assembly 300 engages with the seal 200 and the cross section 100A of handpiece 100.

Ultrasonic driver assembly 300 includes a piezoelectric stack 312 that converts electrical energy into mechanical energy by expanding and contracting. The piezoelectric stack 312 expands and contracts at a frequency that creates ultrasonic vibrational energy, which is transmitted longitudinally through ultrasonic driver assembly 300.

Figure 6:
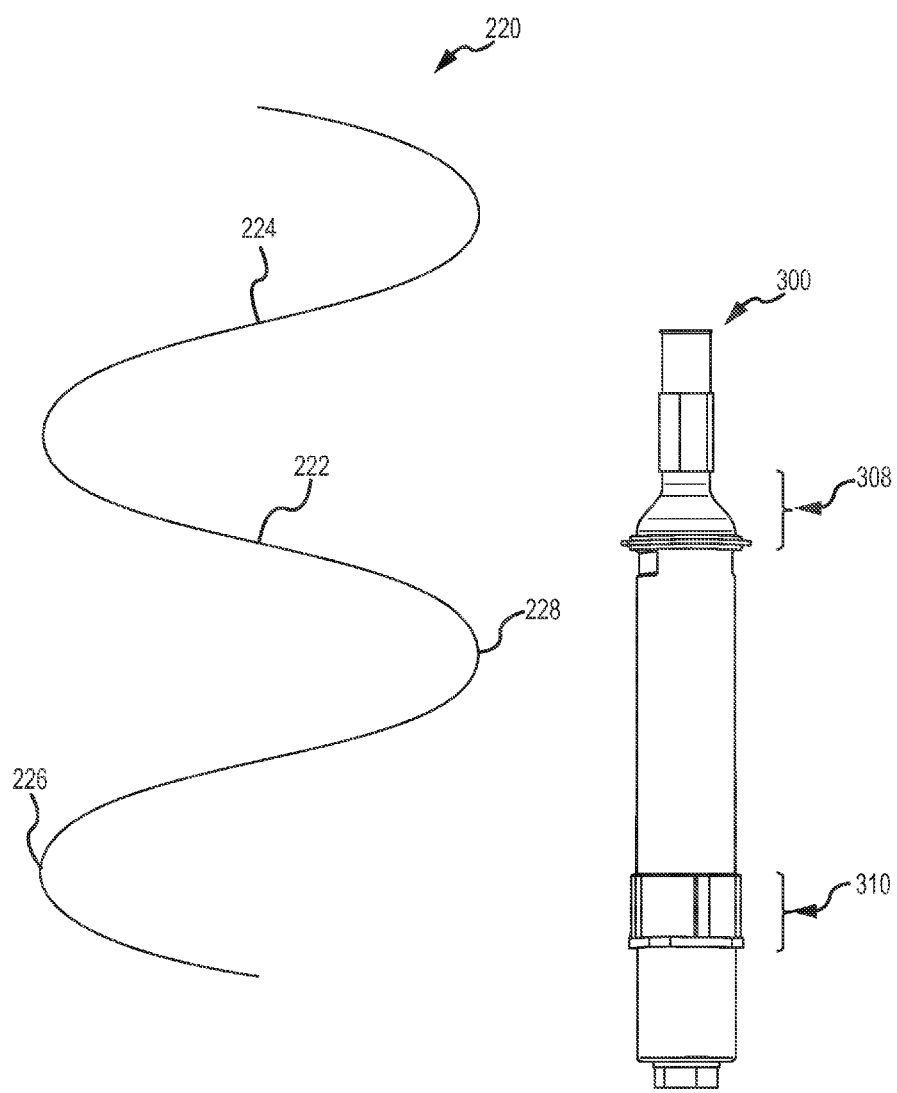
FIG. 6 illustrates an ultrasonic driver assembly shown in FIG. 5 juxtaposed to a wave illustrating vibrational energy transmitted through the ultrasonic driver assembly.

Referring now to FIG. 6, shown is driver assembly 300 and a wave 220 that illustrates the vibrational energy transmitted through ultrasonic driver assembly 300. Wave 220 includes nodes 222 and 224 and antinodes 226 and 228. The nodes are locations where the longitudinal ultrasonic vibration has a maximum amplitude and the antinodes are where the longitudinal ultrasonic vibration has minimal amplitude. Location 308 on driver assembly 300 corresponds to a node location, while location 310 corresponds to an antinode location. In embodiments, ultrasonic driver assembly 300 is held within handpiece 100 at a node location. For example, as illustrated in FIG. 5 node location 308 is the location where ultrasonic driver assembly 300 is held by ridges 110, 112, and 114 in cross-section 100A and within handpiece 100. At node location 308, ultrasonic driver assembly 300 includes a ridge 303, notches 302 in ridge 303, and flat areas 304. Ridge 303 is used to hold ultrasonic driver assembly 300 within handpiece 100A. Notches 302 and flat areas 304 are used to limit the rotation of ultrasonic driver assembly 300.

When handpiece 100 is assembled, seal 200 contacts inner surface 108. Specifically, seal 200 is positioned within channel 111 (FIG. 2). Notch 202 in seal 200 accommodates ridge 114 on inner surface 108. With respect to ultrasonic driver assembly 300, ridge 303 is positioned within channel 204 of seal 200. One of the notches 302 engages ridge 114 on inner surface 108, such that at least a portion of ridge 114 is within notch 302.

The use of seal 200 between inner surface 108 and ultrasonic driver assembly 300 mechanically isolates driver assembly 300 from side wall 102. Thus, ultrasonic driver assembly 300 can freely vibrate within handpiece 100. Further, the anti-rotation mechanism of ridge 114 positioned at least in part within one of the notches 302, limits the rotation of ultrasonic driver assembly 300 within handpiece 100. As an additional anti-rotation mechanism, one of the flat areas 304 is opposed to flat area 116 on second ridge 112. The two flat areas are spaced, and in some embodiments may be in contact, so that they limit the rotation of the ultrasonic driver assembly within handpiece 100. The combination of the two anti-rotation mechanisms significantly limits the rotation of driver assembly 300. Accordingly any wires connected to drive ultrasonic driver assembly 300, will not twist when on ultrasonic probe is being connected and disconnected to ultrasonic driver assembly 300.

It should be understood that the use of ridge 114 positioned at least in part within one of the notches 302 and the flat area 304 engaged with flat area 116 on second ridge 112 are only some examples of anti-rotation mechanisms that may be used in embodiments of the present invention. In other embodiments, the anti-rotation mechanism may include other designs that use notches and ridges. For example, in one embodiment, the notches may be on the inner surface of side wall 102, while the ridges that fit into the notches may be on the driver assembly. In other embodiments, the anti-rotation mechanism may instead rely on a number of flat areas of the housing engaged with flat areas on the driver assembly to prevent rotation of the driver assembly with respect to the housing.

As indicated above, handpiece 100 may be used with an ultrasonic probe that is connected to ultrasonic driver assembly 300. The ultrasonic probe in one embodiment has threads that are engaged with threads 316 on ultrasonic driver assembly 300. The ultrasonic probe is screwed into threads 316. The anti-rotation mechanism (ridge 114 positioned at least in part within one of the notches 302 and the flat area 304 engaged with flat area 116) limits the rotation of assembly 300 when the ultrasonic probe is being screwed into threads 316. In some embodiments, the anti-rotation mechanism is designed to resist rotation of assembly 300 up to 90 in/lbs of torque. Those with skill in the art will appreciate that the anti-rotation mechanism may be designed to withstand larger, or smaller, amounts of torque depending on the particular needs of the medical device.

The node location where driver assembly 300 is held and, where there is an anti-rotation mechanism, is in embodiments located away from base 306 of ultrasonic driver assembly 300. Some ultrasonic driver assemblies place a compressive pre-load on the piezoelectric stack 312. The stack is essentially compressed using a bolt at base 306. Holding ultrasonic driver assembly 300 at this location, or including an anti-rotation mechanism at this location, may interfere, such as by loosening the bolt, with the load being placed on piezoelectric stack 312. For this reason, in embodiments, the node selected for holding driver assembly 300 and locating an anti-rotation mechanism is located away from base 306.

Figure 7:
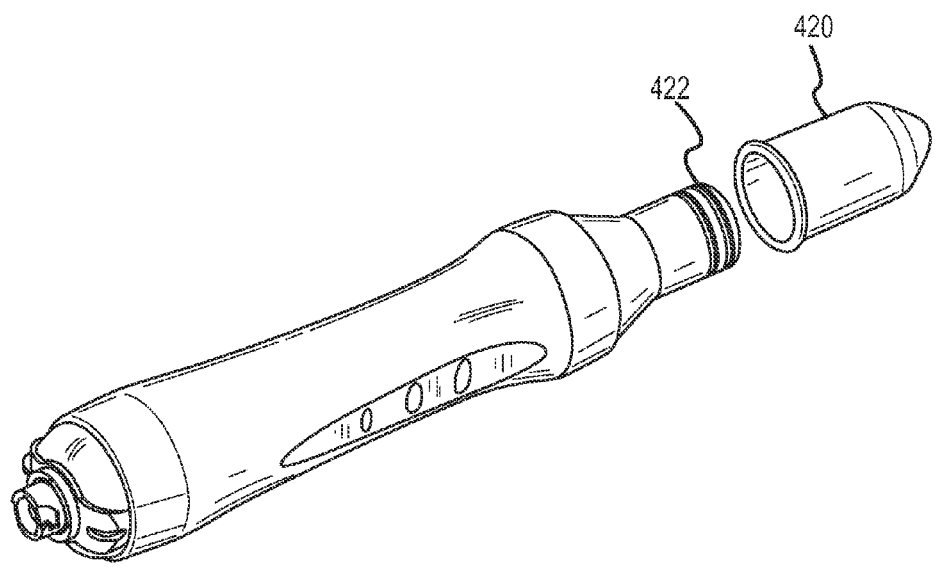
FIG. 7 illustrates a handpiece according to another embodiment of the present invention.
Figure 8:
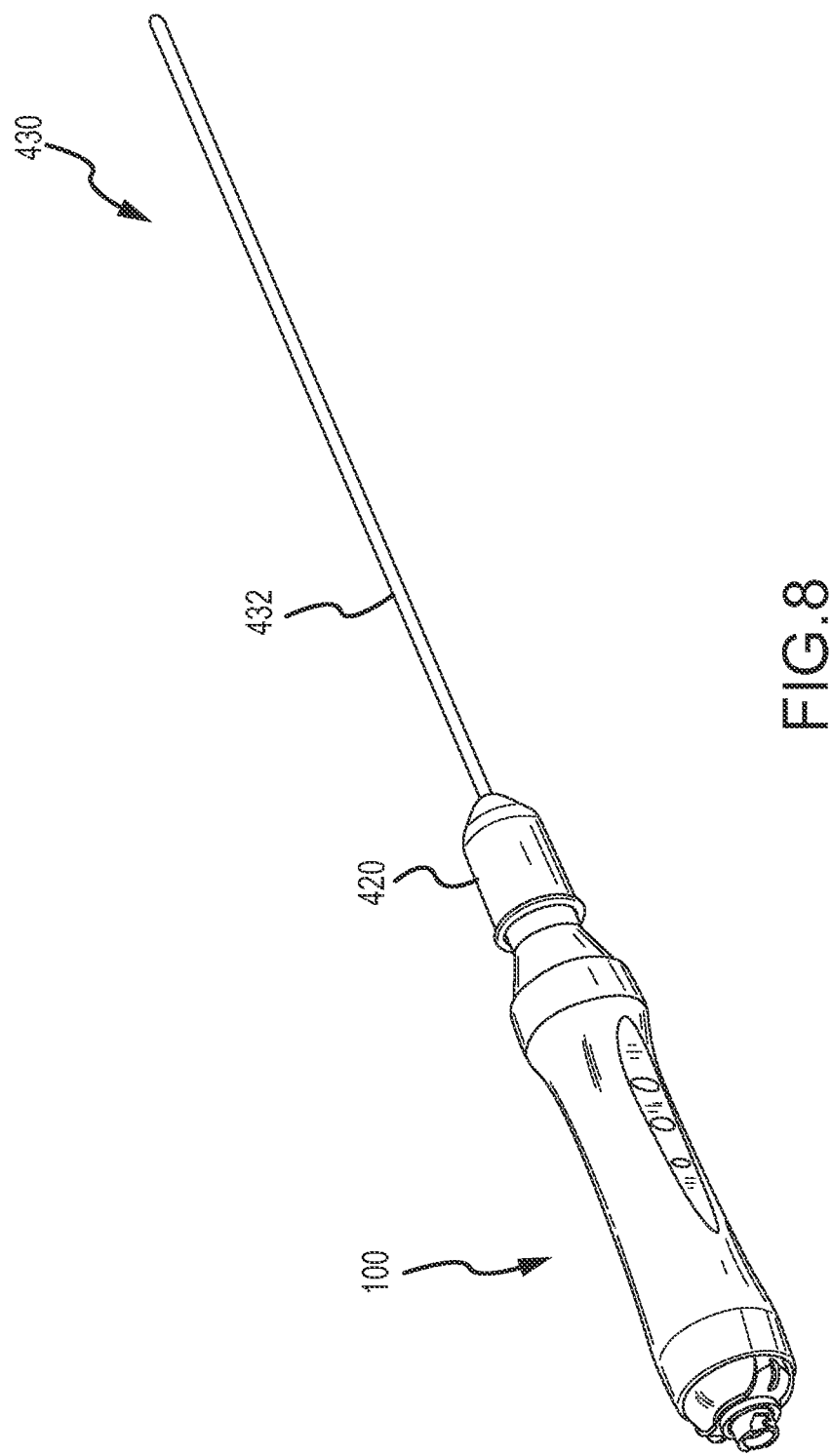
FIG. 8 illustrates an ultrasonic probe assembly, including a handpiece according to an embodiment of the present invention and an ultrasonic probe, as may be used in a lipoplasty procedure.
Figure 9:
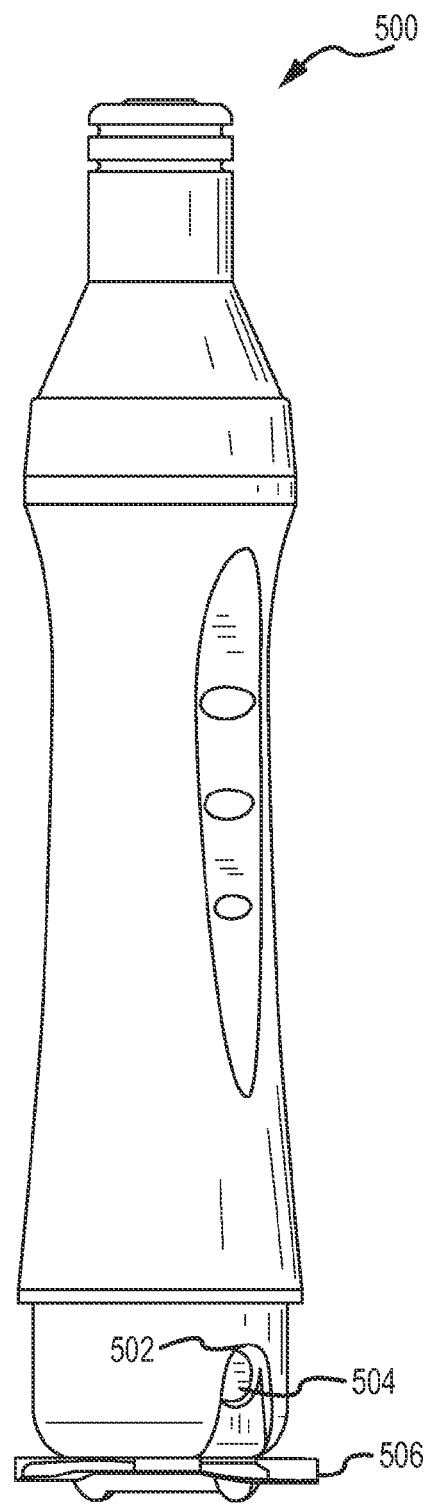
FIG. 9 illustrates a handpiece with a vent and membrane, according to an embodiment of the present invention.

Referring now to FIG. 7, another embodiment is shown with a nosecone 420. Nosecone 420 is used to cover a portion of an ultrasonic probe that is connected to ultrasonic driver assembly 300. Nosecone 420 is used to prevent tissue or other fluids from entering handpiece 100 through the distal end 106. Nosecone 420 engages with an O-ring 422 positioned around the distal end 106 of handpiece 100. Nosecone 420 slides on and off the distal end 106 of handpiece 100. In some conventional designs, nosecones are designed for probes of specific sizes. As a result, a number of different nosecones are required. In contrast, the ability of nosecone 420 to slide allows it to accommodate probes of different sizes. FIG. 8 illustrates an assembled ultrasonic probe assembly 430 that includes handpiece 100, nosecone 420 and a probe 432. FIG. 12 illustrates another embodiment of an assembled ultrasonic probe assembly 630 that includes handpiece 600, nosecone 620 and a probe 632. Assembly 630 has a different nosecone design than shown in FIG. 8. As FIGS. 2-8 illustrate, embodiments of the present invention advantageously provide a handpiece 100 with an anti-rotation mechanism that limits the rotation of medical device components, such as ultrasonic driver assembly 300. This prevents wires that are connected to the medical device components from twisting and/or shorting. Although a specific example of an anti-rotation mechanism is described above, the present invention is not limited to the specific mechanism described above, and may in other embodiments include other combinations of notches, ridges, and flat areas that provide anti-rotation functionality. FIG. 9 illustrates another embodiment of the present invention. FIG. 9 illustrates a handpiece 500 that is hollow and includes an interior volume to house various components. Typically reusable medical devices, such as this, are subjected to an autoclaving, in addition to other sterilization processes, to sterilize the device before reuse. The autoclave cycle uses high-pressure steam to kill microorganisms such as viruses and bacteria. The medical device is then subjected to a drying cycle to remove any trapped moisture from the steam used in the autoclave cycle.

As alluded to previously, several problems have been encountered with the autoclaving-drying process. The autoclaving process must be conducted thoroughly to achieve sterilization, and the drying process must also be conducted thoroughly to prevent harm to sensitive components of the equipment and to avoid leaving residual moisture content for the growth of bacteria. All of this takes time, which limits prompt re-use of the handpiece. In some instances that process may be lengthened by the requirement of disassembling and re-assembling the handpiece to obtain proper sterilization and/or drying which further extends the downtime. Despite care taken in these sanitation processes, the introduction of moisture in the form of both steam and condensed water can have deleterious effects on the components of the handpiece.

In the embodiment shown in FIG. 9, the handpiece 500 includes a vent 502 and a membrane 504 positioned over an opening of the vent 502. Membrane 504 is permeable to vapor to allow steam to flow into (during autoclaving) and out of (during drying) the interior volume of handpiece 500. This allows steam to thoroughly clean the handpiece during autoclaving and to exit the interior volume of handpiece 500 during the dry cycle to substantially eliminate trapped moisture. Preferably the vent and membrane are positioned so that steam can access the interior of the handpiece to achieve sanitation.

Membrane 504 also prevents liquids such as water or other cleaning solutions that may be used to clean handpiece 500 from entering interior volume of handpiece 500. For example, handpiece 500 may be submerged in a cleaning solution and membrane 402 would prevent the cleaning solution from entering the interior volume. Preventing liquid from entering interior volume protects medical device components positioned within handpiece 500 from damage such as corrosion that may be caused by retaining liquid within handpiece 500.

Vent 502 and membrane 504 reduce the amount of time necessary for both the autoclaving and drying cycles since steam is allowed to more quickly enter and exit interior volume of handpiece 500 thereby accommodating a more thorough cleaning of the device. The use of the vent and membrane may also eliminate disassembly and reassembly of the device.

In some embodiments membrane 504 is made from a porous hydrophobic material such as polytetrafluoroethylene (PTFE) sold under the trademark GORE-TEX by W. L. Gore & Associates of Newark, Del. or Fluoropore™ membrane filter distributed by Millipore of Billerica, Mass. In other embodiments, the membrane is made from other materials with 0.3-0.5 micron (µm) pores. PTFE (on a substrate) has properties such as high temperature, low moisture absorption characteristics suited for use as the membrane. Other materials with pore sizes between about 0.3 µm and about 1.5 µm, such as about 1 µm, high temperature capabilities, and low moisture absorption could be used. In one specific embodiment, the membrane 504 is made from a polytetrafluoroethylene material that includes 1 µm pores.

Figure 10:
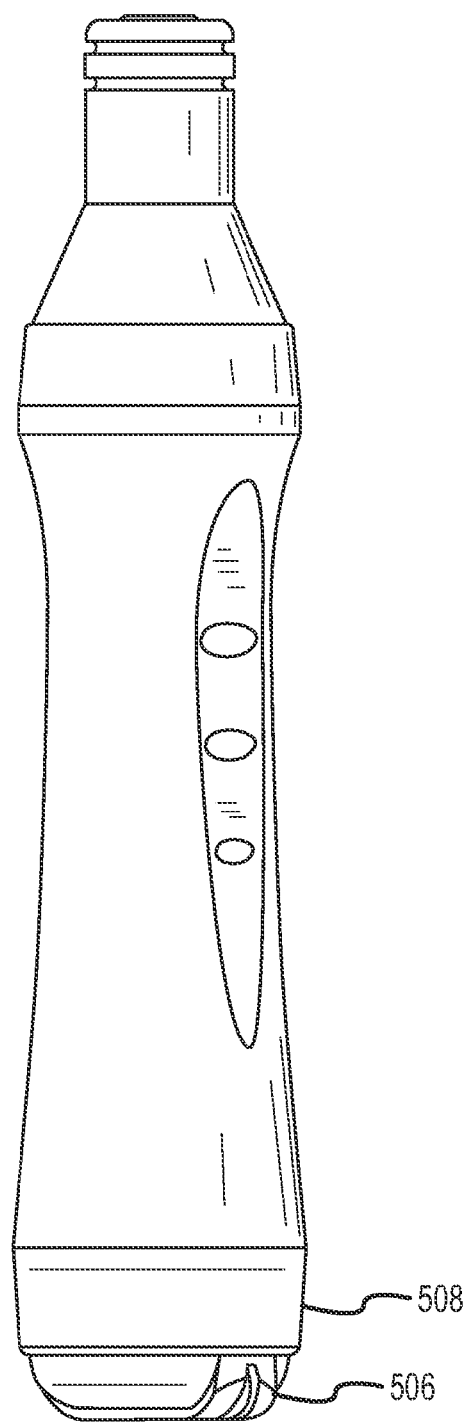
FIGS. 10 and 10A illustrates the handpiece of FIG. 9 with an additional ring that provides some protection for the membrane.

In some embodiments, as shown in FIG. 9, handpiece 500 includes a plug 506 that may be positioned to cover an outside opening of vent 502. FIG. 10 shows plug 506 positioned to cover an outside opening of vent 502. This position is useful when handpiece 500 is in use. Plug 506 prevents potential contaminants (solids and liquids) from collecting in vent 502. During an autoclave or drying cycle plug 506 may be positioned away from vent 502 as illustrated in FIG. 9 to allow steam to enter and exit the interior volume of handpiece 500.

Figure 10A:
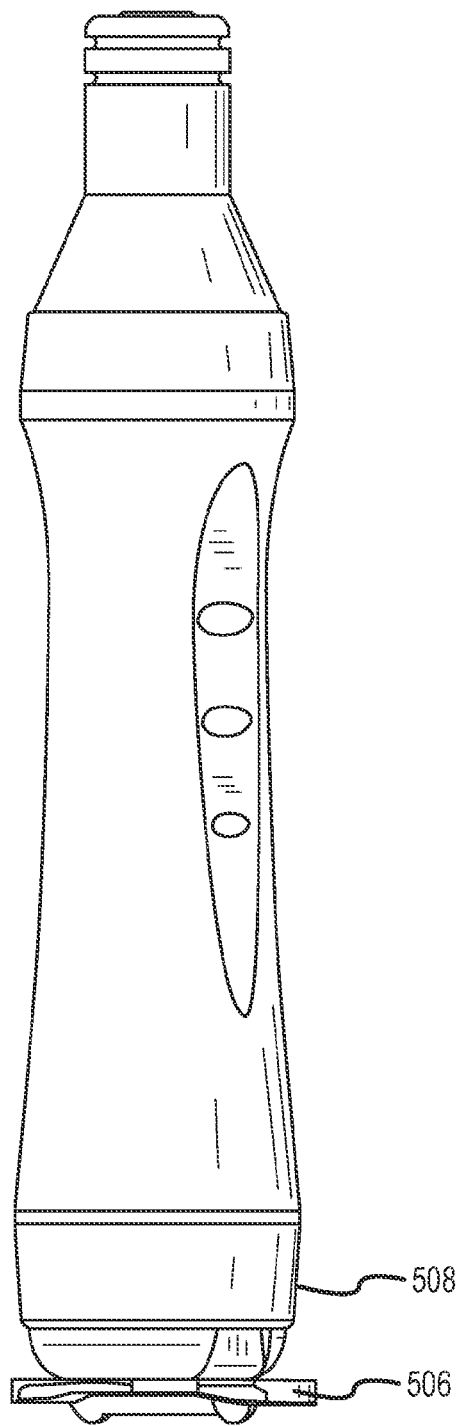

FIG. 10 also shows a ring 508 that partially shields vent 502. Ring 508 is positioned around handpiece 500. Ring 508 provides some protection to membrane 504 from being punctured inadvertently when plug 506 is not positioned to an opening of vent 502 as shown in FIG. 10A. For example, handpiece 500 may be cleaned with a brush to remove contaminants that may be on the handpiece 500 as a result of use during a surgical procedure. The ring 508 would partially shield membrane 504 from the brush and prevent the brush from puncturing membrane 504. As illustrated in FIG. 10, ring 508 still allows plug 506 to be positioned over an outside opening of vent 502.

Figure 11:
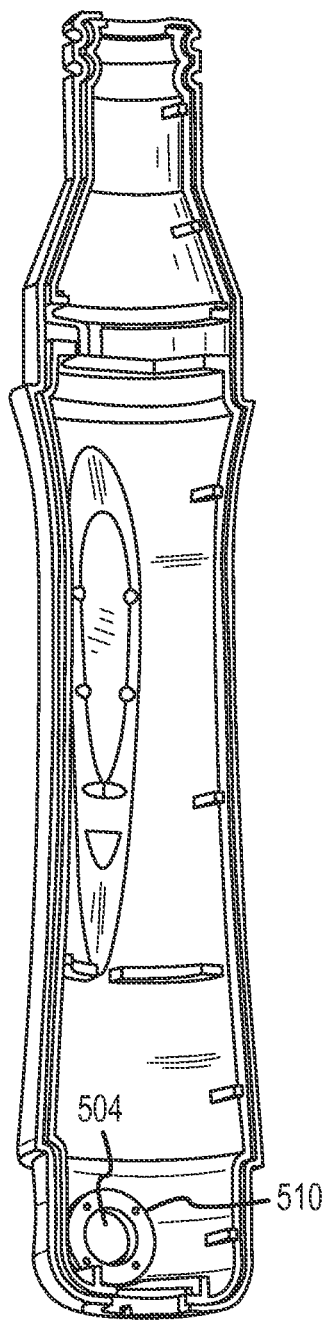
FIG. 11 illustrates a cross section of the handpiece shown in FIG. 9.

Referring now to FIG. 11, a cross-section of handpiece 500 is shown. As shown in FIG. 11, membrane 504 is shown with a ring 510 that snaps into an inside opening of vent 502 to hold membrane 504 in place over an inside opening of vent 502. Ring 510 is one mechanism for maintaining membrane 504 in position over an opening of vent 502. Those with skill in the art with appreciate that other mechanisms may be used to maintain the position of membrane 504 over an opening of vent 502.

Although described in reference to an ultrasonic handpiece, the use of a vent, membrane and protective plug can be incorporated into any medical device where internal components are subjected to autoclaving or similar process for sterilization. One skilled in the art would know how to incorporate those structural components into specific medical devices to facilitate an improved cleaning process.

In one specific embodiment, handpiece 500 may be used as part of an ultrasonic probe assembly for use in ultrasonic assisted lipoplasty. In these embodiments, handpiece 500 may include the features described above with respect to handpiece 100. It should be understood that these are merely some non-limiting examples. In other embodiments, the venting features of handpiece 500 may be used with other types of medical devices that do not necessarily incorporate the features of handpiece 100 described above.

The use of a membrane as discussed above with respect to FIGS. 9-11 are useful in any medical device having an enclosure with an internal volume that contains internal components that may need to be subjected to autoclaving/drying periodically. Such devices could include without limitation, handpieces, aspirators, pumps, electrosurgical units, and ventilators. Any of those devices could be improved by adding an aperture and membrane to facilitate efficient autoclaving and subsequent drying. One or more apertures and membranes can be sized/located at position(s) in the enclosure of the medical device so that the internal components and internal chamber can be sufficiently cleaned when autoclaving steam is applied and can be expeditiously and thoroughly dried during the drying cycle. Optionally, a plug or cover can be employed to protect the membrane and to close the aperture to prevent damage during normal use/storage/transport of the medical device. Accordingly, the embodiments of the present invention described above that include the use of a vent and a gas permeable membrane are not limited to use in a handpiece but have broad application for use in any type of medical device or equipment.

Furthermore, in embodiments, the present invention relates to a method of cleaning and sterilizing a medical device. The method in embodiments includes autoclaving the medical device to provide steam to an internal volume of the medical device. The internal volume includes components of the medical device. In addition, the medical device includes a vent. A membrane that is permeable to steam is positioned over an opening of the vent and allows steam to enter and escape the internal volume through the membrane and the vent. Any suitable autoclave equipment (pressure chambers, heaters, moisture source etc.) for treating medical devices can be used in performing the autoclaving.

After the autoclaving, the medical device is subjected to a drying cycle, which removes moisture from the internal volume of the medical device. The moisture from the internal volume escapes through the vent and the membrane. Any suitable equipment (vacuum chambers, heaters, desiccants, etc.) to dry medical devices can be used in performing the drying cycle.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

What is claimed is:

1. A handpiece for use with an ultrasonic medical device, the handpiece comprising:
    a side wall comprising an inner surface, wherein the side wall extends to form an elongated piece with a proximal end and a distal end;

a first ridge on the inner surface of the side wall, wherein the first ridge is near the distal end of the elongated piece;

a second ridge on the inner surface, wherein the second ridge is parallel to the first ridge and creates a channel between the first ridge and the second ridge;

a third ridge on the inner surface of the side wall and located within the channel; and a seal positionable within the channel and comprising a notch for engaging with the third ridge, wherein the seal is configured to be engaged with an ultrasonic transducer driver assembly at a node other than at the base of the ultrasonic driver assembly to mechanically isolate the ultrasonic driver assembly from the side wall.

2. The handpiece of claim 1, further comprising:

the ultrasonic driver assembly positioned within an interior volume created by the side wall.

3. The handpiece of claim 2, wherein the ultrasonic driver assembly comprises a notch within which at least a portion of the third ridge is positioned, the third ridge and the notch limiting the rotation of the ultrasonic driver assembly.

4. The handpiece of claim 3, wherein at least one of the first ridge and the second ridge comprises a first flat area.

5. The handpiece of claim 4, wherein the ultrasonic driver assembly comprises a second flat area that is opposed to the first flat area.

6. The handpiece of claim 1, wherein the side wall is comprised of two halves connected together.

7. The handpiece of claim 6, wherein the halves are secured together with a ring positioned around both halves.

8. The handpiece of claim 6, wherein the halves are made of a polymer and are solvent welded together.

* * * * *